United States Patent
Gupta et al.

(10) Patent No.: US 10,492,744 B2
(45) Date of Patent: Dec. 3, 2019

(54) SYSTEM AND METHOD FOR MOTION-FREE COMPUTED TOMOGRAPHY

(71) Applicant: THE GENERAL HOSPITAL CORPORATION, Boston, MA (US)

(72) Inventors: Rajiv Gupta, Wayland, MA (US); Yongjin Sung, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 117 days.

(21) Appl. No.: 15/320,616

(22) PCT Filed: Jul. 8, 2015

(86) PCT No.: PCT/US2015/039519
§ 371 (c)(1),
(2) Date: Dec. 20, 2016

(87) PCT Pub. No.: WO2016/007605
PCT Pub. Date: Jan. 14, 2016

(65) Prior Publication Data
US 2017/0196522 A1    Jul. 13, 2017

Related U.S. Application Data

(60) Provisional application No. 62/021,848, filed on Jul. 8, 2014.

(51) Int. Cl.
*H05G 1/30* (2006.01)
*G01N 23/04* (2018.01)
(Continued)

(52) U.S. Cl.
CPC ............ *A61B 6/4014* (2013.01); *A61B 6/032* (2013.01); *A61B 6/0407* (2013.01);
(Continued)

(58) Field of Classification Search
CPC ..... A61B 6/4429; A61B 6/032; A61B 6/4452; A61B 6/027; A61B 6/4028; A61B 6/5235;
(Continued)

(56) References Cited

U.S. PATENT DOCUMENTS 7,706,499 B2    4/2010 Pack et al.
8,077,926 B2    12/2011 Ruimi et al.
(Continued)

OTHER PUBLICATIONS

International Search Report and Written Opinion under dated Oct. 1, 2015 in connection with PCT/US2015/039519.

*Primary Examiner* — Don K Wong
(74) *Attorney, Agent, or Firm* — Quarles & Brady LLP

(57) ABSTRACT

A system and method for computed tomography (CT) imaging is provided. The system includes a gantry having a first and second circumference defining locations fixed in relation to a subject arranged therein, the first and second circumference being axially separated, and spaced from a central axial plane of the gantry. The system also includes a plurality of source modules arranged at locations along the first circumference, and configured for directing X-ray beams toward the subject using a selected illumination pattern, and a plurality of detector modules arranged at locations along the second circumference, wherein the source and detector modules are angled toward the central axial plane such that each source module is diametrically opposed to one or more detector modules. The system further includes an acquisition system configured for controlling the plurality of source modules in accordance with the selected illumination pattern, and acquiring CT image data from the plurality of detector modules.

22 Claims, 6 Drawing Sheets

(51) Int. Cl.
  *G01V 5/00*        (2006.01)
  *A61B 6/00*        (2006.01)
  *A61B 6/03*        (2006.01)
  *A61B 6/04*        (2006.01)

(52) U.S. Cl.
  CPC .......... *A61B 6/4007* (2013.01); *A61B 6/4241* (2013.01); *A61B 6/4291* (2013.01); *A61B 6/4429* (2013.01); *A61B 6/482* (2013.01); *A61B 6/5205* (2013.01); *A61B 6/5282* (2013.01); *A61B 6/5264* (2013.01)

(58) Field of Classification Search
  CPC ............... A61B 6/02; G01N 2223/419; G01N 2223/419; G01V 5/005
  See application file for complete search history.

(56) References Cited

U.S. PATENT DOCUMENTS

| | | |
|---|---|---|
| 2005/0213710 A1 | 9/2005 | Lawrence et al. |
| 2013/0028372 A1* | 1/2013 | Morton .................. A61B 6/032 378/12 |
| 2013/0083886 A1 | 4/2013 | Carmi et al. |

\* cited by examiner

-PRIOR ART-

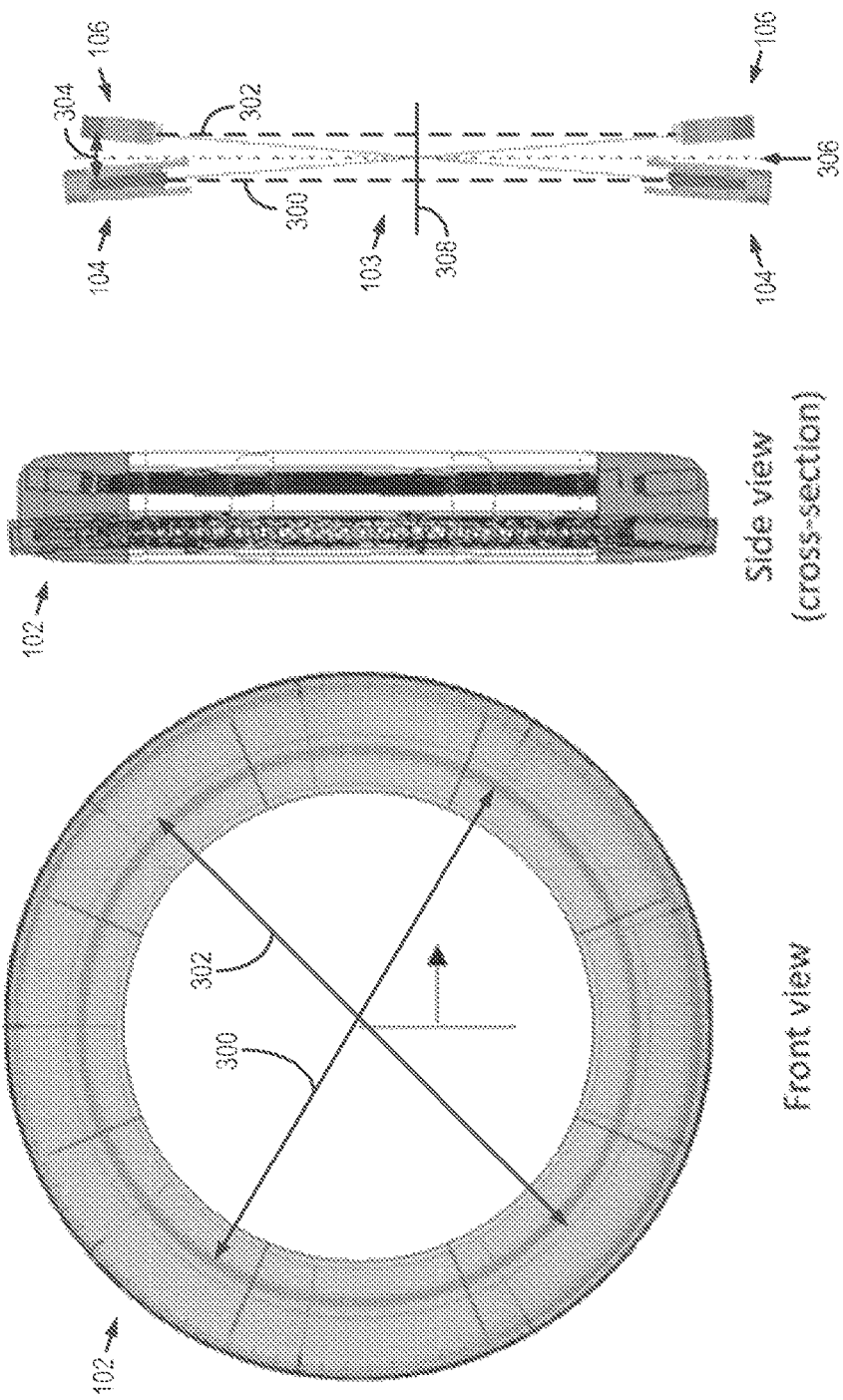

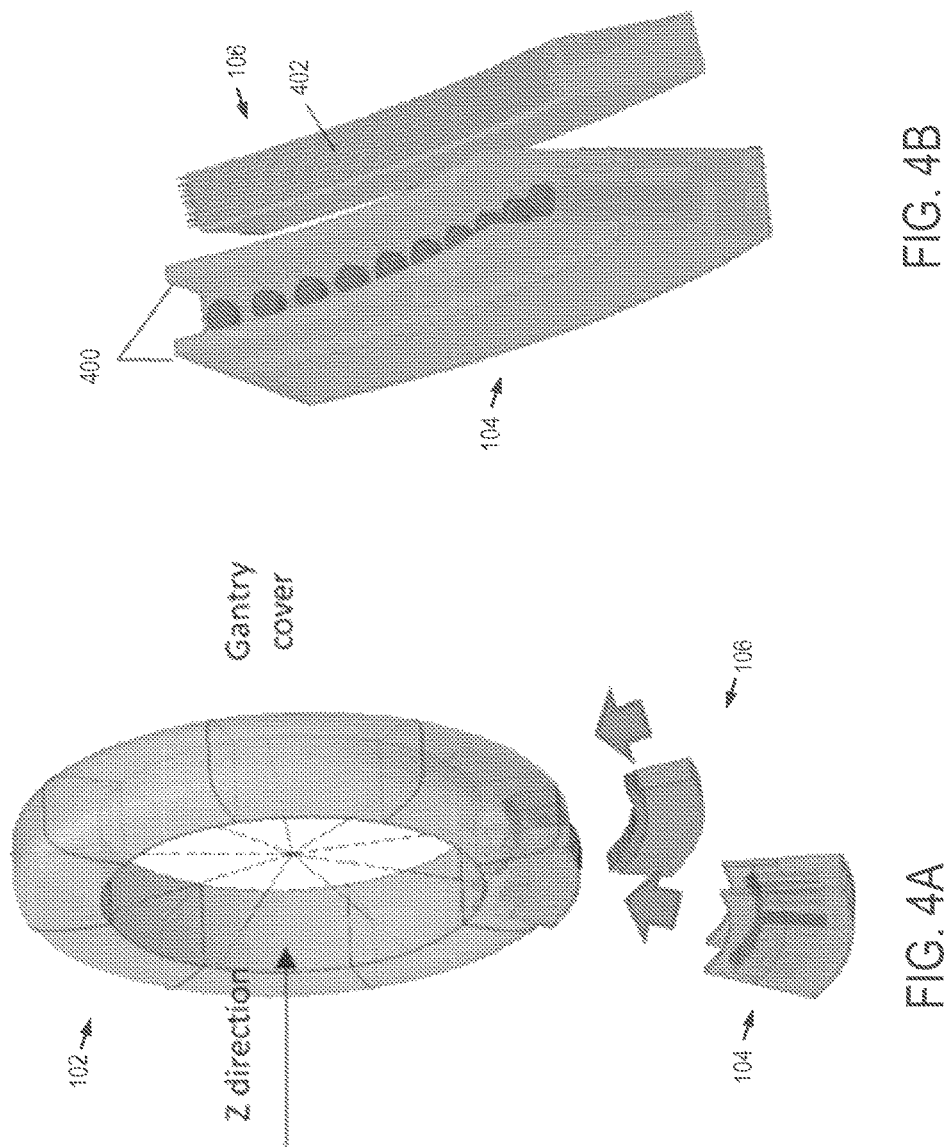

SYSTEM AND METHOD FOR MOTION-FREE COMPUTED TOMOGRAPHY

CROSS-REFERENCE TO RELATED APPLICATIONS

The present application represents the national stage entry of PCT International Patent Application PCT/US2015/039519 filed Jul. 8, 2015, which claims priority to U.S. Provisional Patent Application No. 62/021,848, filed Jul. 8, 2014, the entire contents of which are hereby incorporated by reference.

GOVERNMENT RIGHTS

This invention was made with government support under N66001-11-4204 awarded by the Department of Defense. The government has certain rights in the invention.

BACKGROUND

The present disclosure relates generally to systems and methods for imaging a subject and, in particular, to systems and methods for performing computed tomography (CT) imaging without need for rotation capabilities.

Computed tomography is one of the most common diagnostic imaging modality used in modern medicine, enabling rapid, non-invasive image acquisition at high resolution. However, as shown in the example diagram of FIG. 1A, conventional CT systems 10 generally include a gantry 12 fitted with a single X-ray tube 14 (or at most, two X-ray tubes for systems currently in clinical use, not shown) and opposing detector assembly 16, which, together, rotate about a subject 18 to acquire multiple projections for reconstructing an image. That is, the X-ray tube 14 and detector assembly 16 arranged opposite the X-ray tube 14 are affixed to the gantry 12 and rotate together with the gantry 12 about the subject 18. As illustrated in the picture of FIG. 1B, this architecture is complex and requires heavy and sophisticated control hardware and electronics, which increases the cost and limits availability in developing countries, or in resource-limiting environments, such as a battlefield. In addition, the temporal resolution attained using conventional CT systems is also limited by the time required for the gantry to mechanically complete a significant portion of an angular rotation. As a result, the reduced temporal resolution amplifies motion artifacts due to breathing or involuntary motion of a patient, affecting the spatial resolution achievable and degrading the quality of the reconstructed image.

In attempts to overcome such limitations, introduced "fifth generation" CT designs have avoided use of a rotating gantry in lieu of stationary components. In particular, such CT systems include a fixed electron emitter along with elements for directing a generated electron beam to multiple anode strips partially occupying a gantry encircling the patient. Generated X-ray beams traversing the patient are then detected by a detector array occupying the remainder of the gantry. Although capable of fast scanning, such CT systems require steering of energetic electron beams along the circumference of gantry, suffer from limited photon flux, and may not cover a full 360 degree angle perspective of the patient. In addition to a large system footprint, fifth generation CT scanners are also associated with high costs and are difficult to calibrate, thus limiting their practical application. Furthermore, in existing stationary and non-stationary CT system designs, a small failure in one of the components renders the entire system to be inoperable.

Therefore, given the above, there is a need for systems capable of fast and accurate computed tomography imaging that is not so limited by complexity and size.

SUMMARY

The systems and methods of the present disclosure overcome the aforementioned drawbacks by providing a systems for computed tomography (CT) imaging implementing a modular design including multiple X-ray sources and detectors distributed around a subject to be imaged. A rotation-free imaging system is achieved, whereby multiple X-ray source and detector modules are distributed along separate rings of a CT system gantry at locations fixed in relation to an examination subject or object arranged therein, and oriented such that each X-ray source pairs with one or more detector elements. The X-ray source modules may then irradiate the object uniformly, or in a time-varying fashion, using a selected pattern, thus enabling tomographic reconstruction from a smaller number of projection images than used in conventional CT and without rotation. By removing the necessity of a rotating gantry, the CT system can be manufactured with reduced weight, cost, and complexity. In addition, the static nature of the proposed system also enables modular design of the X-ray generation and detection parts, thus facilitating the system to be more robust upon failure or damage of some components. Furthermore, installing multiple detector modules on the circumference of the gantry, the system can capture the Thomson and Compton X-ray scattering components from the object, which are not available in conventional CT. Finally, the system can be used to perform dual energy CT without installing specialized electronics.

In accordance with one aspect of the disclosure, a computed tomography (CT) imaging system is disclosed that includes a gantry having a bore for receiving a subject for imaging and defining a central axis extending along the bore and a radial plane extending transversely to the central axis extending along the bore. The system also includes a plurality of source modules coupled to the gantry at fixed radial locations about the bore for directing X-ray beams toward the subject arranged in the bore and a plurality of detector modules coupled to the gantry at fixed radial locations about the bore such that one of the plurality of detector modules is arranged in diametric opposition to and on opposite sides of the radial plane of one of the plurality of source modules. The system further includes a control system configured to control the plurality of source modules to perform an imaging process with respect to the subject to receive CT image data from the plurality of detector modules.

A system for computed tomography (CT) imaging is provided. The system includes a gantry having a first and second circumference defining locations fixed in relation to a subject arranged therein, the first and second circumference being axially separated, and spaced from an axial plane of the gantry. The system also includes a plurality of source modules arranged at locations along the first circumference, and configured for directing X-ray beams toward the subject using a selected illumination pattern, and a plurality of detector modules arranged at locations along the second circumference, wherein the source and detector modules are angled toward the axial plane such that each source module is diametrically opposed to one or more detector modules. The system further includes an acquisition system configured for controlling the plurality of source modules in accordance with the selected illumination pattern, and acquiring CT image data from the plurality of detector modules.

The foregoing and other advantages of the invention will appear from the following description.

BRIEF DESCRIPTION OF THE DRAWINGS

FIG. 3A illustrates the frontal and side (cross-section) views of an example motion-free CT gantry design, in accordance with the present disclosure.

FIG. 3B is a schematic depicting a cross-sectional view of a source-detector geometrical arrangement, in accordance with aspects of the present disclosure.

FIG. 4A is an illustration of an example modular design, accordance with aspects of the present disclosure, showing the insertion of source and detector modules into the gantry.

FIG. 4B is a detailed of illustration of the source and detector modules shown in FIG. 4B.

DETAILED DESCRIPTION

Figure 1B:
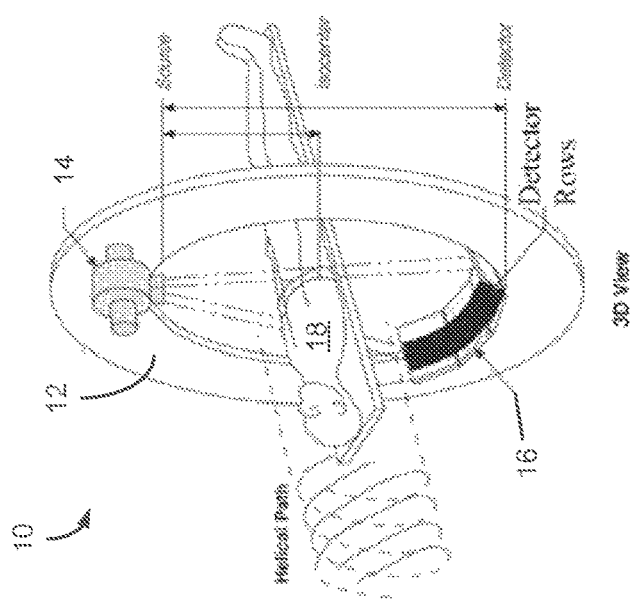
FIG. 1B is a picture of open gantry of a flat-panel detector based CT shows packed heavy electronics mounted on slip rings.
Figure 1A:
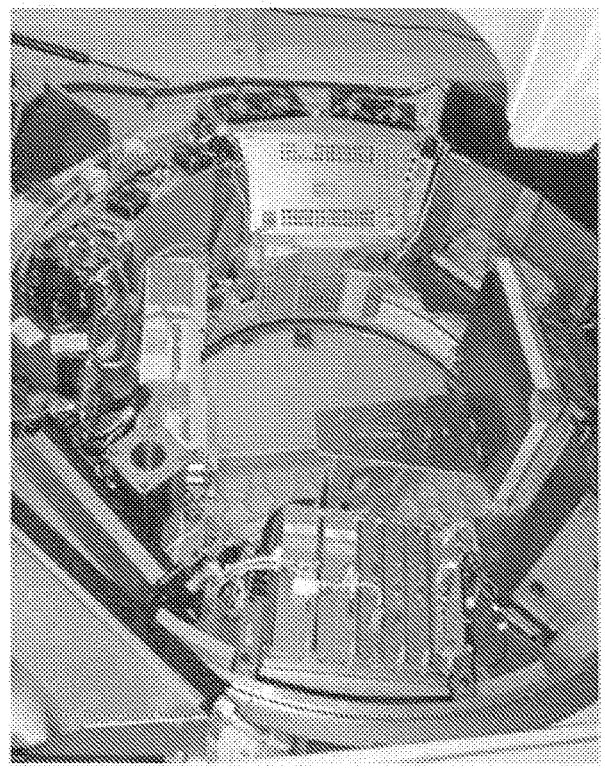
FIG. 1A is a schematic illustrating a conventional rotating-gantry CT scanner with an X-ray source paired with a detector that revolves around the object along a circular trajectory while taking multiple projection images.

Tomographic reconstruction of a cross-sectional image generally includes acquiring multiple projection images at different illumination angles with respect to an imaged object. In conventional CT, the illumination angle is varied by rotating an X-ray source and a detector array around the imaged object. Generally, in order to minimize motion artifacts, a full scanning is completed in a fraction of second, during which more than 1000 projection images are typically recorded. For accurate image reconstruction, both large angular coverage and a fine angular step are important. Therefore, conventional approaches for performing CT imaging necessitate highly sophisticated controls for the source, detectors, as well as electronics optimized for a rotatable architecture. In addition, in order to generate high signal-to-noise ratio (SNR) projection images within a small time period, a high tube current for the X-ray source, and high frame rate of data acquisition are needed, requiring heavy cooling mechanisms and expensive electronics, respectively. Importantly, in conventional CT system designs, each component is given a dedicated function, e.g., a source for X-ray generation and a detector for X-ray detection. Thus, a small failure in one of the components renders the entire CT imaging system to be inoperable. As will be described, to overcome these limitations, the present disclosure provides a motion-free CT system using the concept of modular design, and distributing X-ray sources and detectors in a novel way along the circumference of the gantry.

As will be described, the systems and methods of the present disclosure are conceptually different form the existing CT imaging techniques in that a design is adopted that includes multiple X-ray sources and detectors instead of rotating a pair of source and detector to perform tomographic CT imaging. By installing the source and detector modules at a slanted angle on separate rings, a CT system in accordance with the present disclosure, can achieve full 360 degree angular coverage without a rotating gantry.

In addition to projected X-rays traveling through a subject, scattered X-rays due to Thompson and Compton scattering processes, also contain rich detail about the subject. However, in conventional CT systems designed for measuring linear attenuation, such scattering information is not obtained. By contrast, and in addition to other capabilities afforded by the present disclosure, detector arrangements around a system gantry not only allow acquisition of attenuated X-rays components over a full rotational perspective, but also permit simultaneous capture of scattered X-ray components. Such scattered components can provide additional information for improving image quality without undue complexity, for example, for use in enhancing soft tissue contrast and spatial resolution.

Systems employing multiple modules for source and detector components, in accordance with the present disclosure, may also continue with normal operation even in the case where certain modules may be defective or damaged. This enables robust operation of such systems in resource-limited environments, for example, a developing country or a battlefield. In addition, in some system configurations, multi-energy capabilities may also be implemented by configuring X-ray source components included therein to operate at different tube voltages, or using multiple anode materials, or combinations thereof.

Figure 2A:
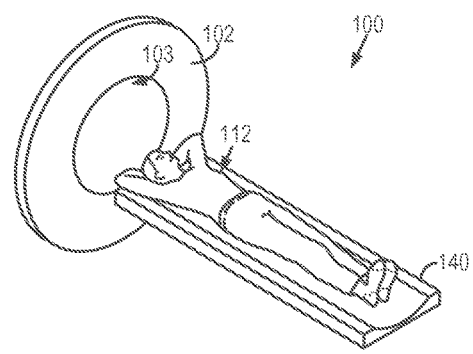
FIG. 2A illustrates an example motion-free CT having a single X-ray source turned on, in accordance with aspects of the present disclosure.
Figure 2B:
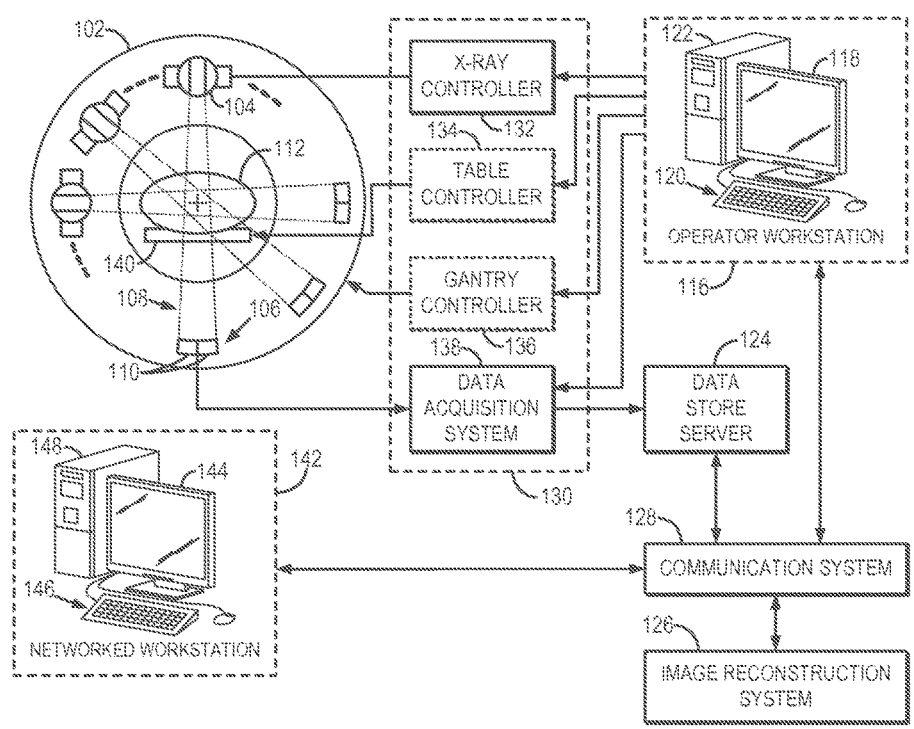
FIG. 2B illustrates an example motion-free CT having multiple X-rays turned on, in accordance with aspects of the present disclosure.

Referring particularly now to FIGS. 2A and 2B, an example of a motion-free x-ray computed tomography (CT) imaging system 100 is illustrated. The CT system 100 includes a gantry 102 that extends about a bore 103. The gantry 102 has multiple X-ray source modules 104 and detector modules 106 that are circumferentially arranged about the gantry 102, and coupled therein in a stationary fashion. That is, positions of the source modules 104 and detector modules 106 are at locations fixed in relation to a subject 112 arranged at a specific position along the gantry 102. The X-ray source modules 104 project an x-ray beam 108, which may be a fan-beam or cone-beam of X-rays, towards respective detector modules 106 on the opposite side of the gantry 102. In certain aspects, the source modules 104 are configured to operate at one or more X-ray energy levels.

The detector modules 106 may include multiple X-ray detector elements 110. For the sake of clarity, however, FIG. 2B only depicts a few X-ray source modules 104 and a few corresponding detector modules 106. Together, the X-ray detector elements 110 sense the projected X-rays 108 that pass through or are scattered by a subject 112, such as a medical patient or an object undergoing examination, that is positioned in the bore 103 of the CT system 100. Each X-ray detector element 110 produces an electrical signal that may represent the intensity of an impinging X-ray beam and, hence, the attenuation or scattered components of the beam as they passes through or scatter from the subject 112. In some configurations, each X-ray detector 110 may be capable of counting the number of X-ray photons that impinge upon the detector 110. That is, the detector 110 may include photon counting and/or energy discriminating detectors. However, the detector 110 may also include energy integrating detectors.

The CT system 100 also includes an operator workstation 116, which typically includes a display 118; one or more input devices 120, such as a keyboard and mouse; and a computer processor 122. The computer processor 122 may include a commercially available programmable machine running a commercially available operating system. The operator workstation 116 provides the operator interface that enables scanning control parameters to be entered into the CT system 100. The operator workstation 116 may be in communication with a data store server 124 and an image reconstruction system 126, or the functions of data storage and image reconstruction may be performed on the operator workstation 116. By way of example, the operator workstation 116, data store sever 124, and image reconstruction system 126 may be connected via a communication system 128, which may include any suitable network connection, whether wired, wireless, or a combination of both. As an example, the communication system 128 may include both proprietary or dedicated networks, as well as open networks, such as the internet.

The operator workstation 116 is also in communication with a control system 130 that controls operation of the CT system 100. The control system 130 generally includes an x-ray controller 132 and, optionally, may include a table controller 134, an optional gantry controller 136, and a data acquisition system 138. The X-ray controller 132 provides power and timing signals to respective X-ray source modules 104, in accordance with a desired scanning pattern. In some modes of operation, the X-ray controller 132 may be configured to concurrently operate multiple source modules 104 to achieve a uniform scanning pattern impinging on an object. In other modes of operation, each of the multiple source modules 104 may be operated in a time-varying fashion based on a selected illumination pattern. If included, the table controller 134 controls a table 140 to position the subject 112 in the gantry 102 of the CT system 100. In some situations, the table controller 134 may be mechanically controlled, such as by manually actuated levers or other controls. Furthermore, powered or manual control may be foregone. For example, in some situations, the table 140 may be a stretcher or make-shift table and the patient and table 140 adjusted as needed, such as may occur in battlefield or other deployments. In some alternative configurations, an optional gantry controller 136 may control the position of the gantry 102 with respect to the subject 112.

The DAS 138 samples data from the detector modules 106 and converts the data to digital signals for subsequent processing. For instance, digitized X-ray data is communicated from the DAS 138 to the data store server 124. The image reconstruction system 126 then retrieves the X-ray data from the data store server 124 and reconstructs an image therefrom. The image reconstruction system 126 may include a commercially available computer processor, or may be a highly parallel computer architecture, such as a system that includes multiple-core processors and massively parallel, high-density computing devices. Optionally, as mentioned, image reconstruction can also be performed on the processor 122 in the operator workstation 116. If not reconstructed at the operator workstation 116, reconstructed images can be communicated back to the data store server 124 for storage or to the operator workstation 116 to be displayed to the operator or clinician.

The CT system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 116, or in a different facility, such as a different healthcare institution or clinic.

The networked workstation 142, whether within the same facility or in a different facility as the operator workstation 116, may gain remote access to the data store server 124 and/or the image reconstruction system 126 via the communication system 128. Accordingly, multiple networked workstations 142 may have access to the data store server 124 and/or image reconstruction system 126. In this manner, x-ray data, reconstructed images, or other data may be exchanged between the data store server 124, the image reconstruction system 126, and the networked workstations 142, such that the data or images may be remotely processed by a networked workstation 142. This data may be exchanged in any suitable format, such as in accordance with the transmission control protocol (TCP), the internet protocol (IP), or other known or suitable protocols.

Referring to FIGS. 3A and 3B, a schematic illustration of the gantry 102 of the present disclosure is provided. In contrast to previous designs, arrangement of multiple source modules 104 and detector modules 106 is achieved along separate rings of the gantry 102, by way of a first 300 and second 302 circumference configured in the gantry 102, respectively. As shown in FIG. 3B, the first 300 and second 302 circumference are axially separated by a lateral distance 304, and spaced from a radial plane 306 of the gantry 102 that runs perpendicular or transverse to a central axis 308 of the bore 103. As illustrated, the source modules 104 and detector modules 106 are angled toward the radial plane 306 such that each source module 104 is diametrically opposed to at least one detector module 106, to facilitate capture, among other X-ray beam components, attenuated beam components traversing an object, or subject. That is, each pair of source modules 104 and detector modules 106 includes one source module 104 and diametrically opposed detector module 106 arranged on opposite sides of the radial plane 306.

Additionally, a CT system in accordance with the present disclosure, may utilize multiple modules to enable a normal system operation even when some components are damaged. This feature can be useful in resource-limited environments such as a developing country or a battlefield. For this purpose, a gantry 102 of a system, as described, includes multiple source modules 104 and detector modules 106 that may be redundant and/or can be easily replaced without disintegrating the whole gantry 102. For instance, each source module 106 may be designed to enable easy replacement of damaged X-ray generating elements.

Particularly referring to FIG. 4A, a non-limiting example of the gantry is illustrated. The non-limiting example includes 9 source modules 104 and 9 detector modules 106. However, as may be appreciated, the number of modules may be varied depending on the size of system, targeted spatial resolution and accuracy. In the illustrated example, all modules are omitted, except ones at the bottom of the gantry 102, for clarity. As shown, the source modules 104 and detector modules 106 can be inserted and replaced with new ones upon malfunction or damage in a manner similar to replacement of laser toner cartridges.

Referring now to FIG. 4B, a perspective view of a source module 104 and detector module 106, in accordance with aspects of the present disclosure, is shown. Specifically, each source module 104 may include multiple X-ray source units, for example, 10, although various values may be possible, arranged in a linear array, although other configurations may also be possible. The source modules 104 may include two, or more, layers of shielding elements 400 configured for minimizing an X-ray contamination in proximate detector modules 106 or escaping from the gantry 102. In addition, each source module 104 may further include a source module controller (not shown) in communication with the X-ray controller 132 described. In certain aspects, the source modules 104 may further configured to operate at more than one X-ray energy levels.

As illustrated, the detector module 106 may include a curved detector arranged under an anti-scatter grid 402, although other shape configurations may be possible, and may include multiple layers forming the anti-scatter grid 402. The anti-scatter grid 402 may be fashioned using a variety of suitable materials to block the X-rays scattered along a longitudinal, or Z-direction, while preserving at least some scattering along the other directions. As described, each source module 104 and detector module 106 may be configured along a slanted angle with respect to each other to guarantee that the trajectory of a transmitted X-ray beam from each source hits detector elements diametrically opposed to the object. In addition, each detector module 106 may further include a detector module controller (not shown) in communication with a DAS 138, as described with reference to FIG. 2B.

Figures 5A, 5B:
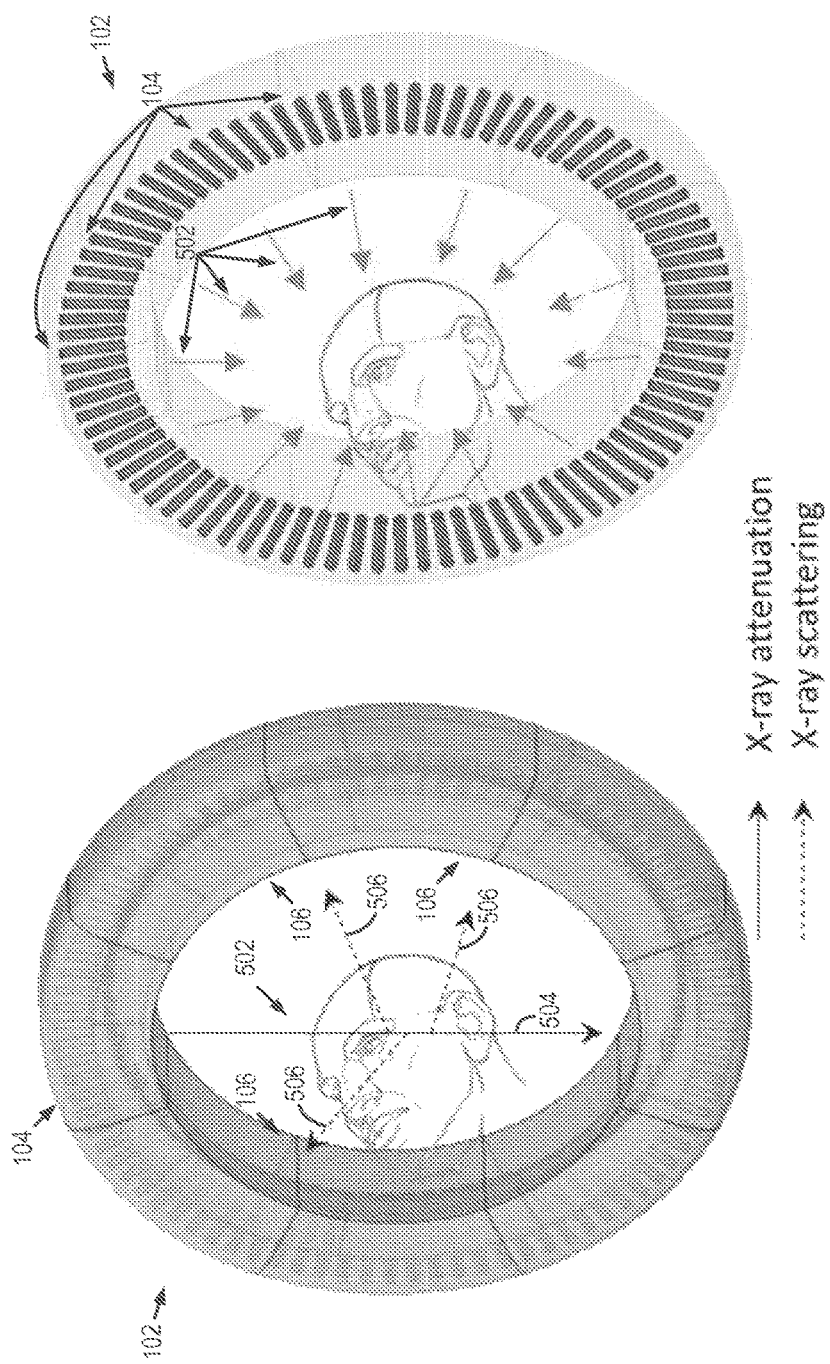
FIG. 5A illustrates an example motion-free CT gantry design, in accordance with the present disclosure, depicting an object illumination using a single source module.
FIG. 5B illustrates another example motion-free CT gantry design, in accordance with the present disclosure, depicting an object illumination using multiple source modules.

Referring to FIGS. 5A and 5B, aspects of a rotation-free CT system in accordance with the present disclosure are shown. As used herein a "rotation-free" CT system refers to a system, such as described herein, where rotation of the gantry is not necessary to perform tomographic imaging. Specifically, FIG. 5A shows the trajectory of an X-ray beam 502 emitted from a single source module 104. As the X-ray beam 502 is incident on the object, which may include a patient or inanimate object, such as a package, some of the X-rays of the X-ray beam 502 pass through the object as an attenuated X-ray beam 504, while other X-rays form scatter 506. By contrast, in conventional CT systems, only the attenuated X-ray beam 504 is measured, while the scattered X-rays 506 are considered as sources of noise. However, the present disclosure recognizes that the scattered x-rays contain information about the object, and can be used to enhance the soft-tissue contrast and increase the spatial resolution. Thus, in accordance with the present disclosure, the scattered X-rays 506 may be collected by the multiple detector modules 106 distributed about the circumference of the gantry 102.

The above-described process can be performed sequentially or in parallel. By way of example, FIG. 5B illustrates one specific scanning pattern, whereby the multiple source modules 104 distributed along the circumference of the gantry 102 are operated simultaneously in order to illuminate the object uniformly. In other modes of operation, the sources modules are operated in a time-varying fashion to achieve a selected illumination pattern. In this manner, multiplexed images can be decoded in a reconstruction step using the known information of system configuration including the illumination pattern. Compressed sensing techniques can then be used to reduce the number of images required for tomographic reconstruction by using a priori information of the object, such as described in U.S. Pat. No. 8,374,413, which is incorporated herein by reference.

The angular step of X-ray scanning mainly depends on the distance between the X-ray source in the detector module. Compressed sensing enables to reconstruct the object from sparse sampling, i.e., projection images acquired with sparsely distributed sources. However, in certain configurations, a finer angular step can be achieved by incorporating a steering system in each source module, configured for directing an electron beam generated therein. Specifically, the steering system may be capable of providing either an electronic steering, a magnetic steering, or an electrostatic steering, as shown in FIGS. 6A, 6B and 6C, respectively.

Figure 6A:
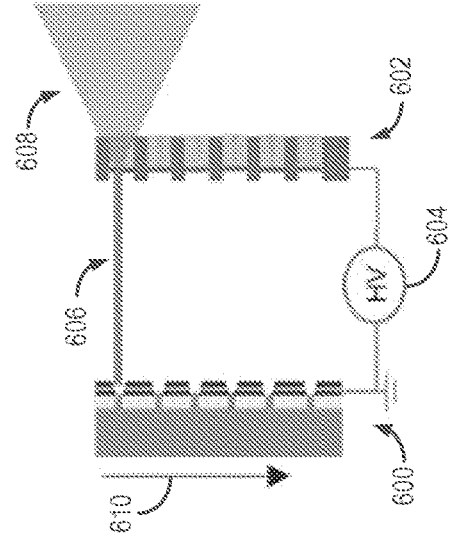
FIG. 6A illustrates example electron beam scanning method for use in an X-ray source, in accordance with the present disclosure, utilizing an electronic method.

In particular, as illustrated in FIG. 6A, a cathode array 600, such as a linear array, may be arranged at a distance from a correspondingly arranged anode array 602, separated by a high-voltage, potential difference. Electrons move from the cathode array 600 along a beam path 606 to the anode array 602, whereby an x-ray beam is created 608. To move or adjust the x-ray beam 608, the cathode array 600 may be selectively energized along the array to move the beam path 606 along a scanning direction 610 and, thereby, correspondingly move the beam path 606 and x-ray beam 608.

Figure 6B:
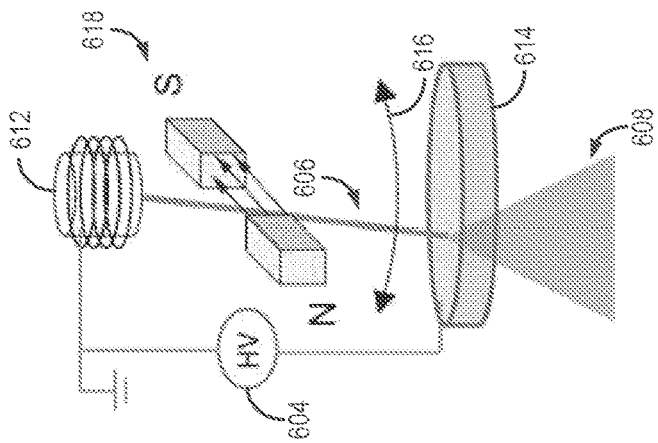
FIG. 6B illustrates another example electron beam scanning method for use in an X-ray source, in accordance with the present disclosure, utilizing a magnetic method.
Figure 6C:
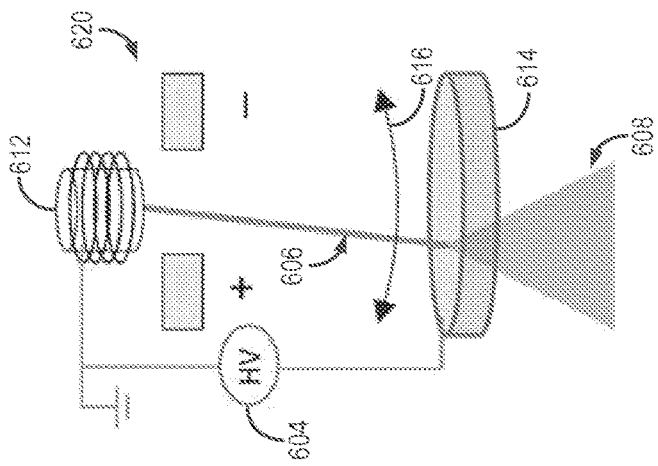
FIG. 6C illustrates yet another example electron beam scanning method for use in an X-ray source, in accordance with the present disclosure, utilizing an electrostatic method.

Referring to FIGS. 6B and 6C, the system includes a cathode 612 arranged at a distance from an anode 614. As illustrated, the anode may be a plate anode 614 or other desirable geometry capable of receiving the electron beam 606 as it as swept or scanned across the anode 614, as generally illustrated by arrow 616, to move the x-ray beam 608 correspondingly. As illustrated in FIG. 6B, movement of the electron beam path 606 may be achieved by magnetically influencing the electron beam path 606 using a magnet system 618. Similarly, as illustrated in FIG. 6C, the electron beam path 606 may be moved by controlling a system 620 for creating a potential difference along the electron beam path 606. Specifically, by adjusting the parameters of the system 620, in \magnitude and/or position, the electron beam 606 can be moved across the anode 614, as indicated by arrow 616, to correspondingly control or move the x-ray beam 608.

Such electron beam steering may recapitulate methods of 5th generation CT, in which electron beams are steered before hitting the annular anode covering a gantry surface. However, the electron beams, in accordance with system designs described herein, can be steered in each source module, providing robustness with respect to failure critical source components.

By virtue of the design described herein, including a distributed array of sources and detector modules, the X-ray attenuation and scattering components may be simultaneously measured. As described, for the attenuation component measurements, the source and detector modules are arranged in a fashion that guarantees that each beam trajectory from each source module crosses certain detector elements. In order to achieve as much angular coverage as possible, the X-ray source and detector modules are installed on separate rings and mounted at a slanted angles so that all X-ray source modules pair with certain detector elements. In this arrangement of sources and detectors, all the sideways and backward scattered X-ray components are naturally collected and processed.

In a conventional rotating-gantry CT scanner, an X-ray source paired with a detector rotates around the imaged object and records multiple projection images. Each projection image can be considered as a line integral of the attenuation coefficients defined on the voxels of the object. Thus, using an algorithm, such as an inverse Radon transform, to reverse this integral, one can obtain a depth-resolved attenuation map for the object, which comprise geometrical and material information, both clinically important. CT reconstruction is then done using various techniques, including analytic inversion, single-step filtered back-projection, iterative reconstruction, and so on. Iterative reconstruction is known to be accurate by using system geometry and a physical model for X-ray-object interaction. The Shannon-Whittaker theorem puts a theoretical limit on the smallest number of sampling to guarantee a complete restoration of a signal or an image. The conventional CT scanner has been designed to conform to this requirement. However, it is now well established that the sampling number can be significantly reduced using a priori information of the object and an accurate model of the imaging process.

By contrast, a system in accordance with the present disclosure, can interrogate an object with X-rays from multiple angles, either simultaneously or in a time-varying fashion, and measure the X-ray attenuation and scattering. As mentioned, a selected illumination pattern can be uniform, i.e., all the sources are switched on, or varying with time, i.e., different subsets of the sources are switched on. In some scenarios, using multiple projection images recorded for time-varying illumination patterns, one can perform tomographic reconstruction in a more robust way than using a single projection image with uniform illumination. In either case, a compressed sensing technique may be combined with detailed system modeling of the imaging geometry and a prior knowledge of a selected illumination pattern to achieve efficient imaging. In particular, a total number of imaged required for tomographic reconstruction will be much less than that required in conventional CT. Hence, using a compressed sensing technique, a significant reduction in the required number of source sources may be achieved, with an increase in robustness when a certain fraction (e.g., 20%) of the sources and detectors are damaged. Specifically, an exact number of required sources and their arrangements can be decided based on the imaging geometry, the categories of imaged object, a required accuracy, and so forth. More importantly, images acquired in a manner described, are generated without any motion of component, overcoming drawbacks of conventional CT.

Therefore, a CT system is provided that includes multiple sources and detector modules. Each source module includes X-ray sources arranged in a linear array and a controller for the module. Each detector module includes a curved detector, controller, and an anti-scatter grid. As described, X-rays may illuminate the object from a full 360 degree angle view, and spatially-multiplexed projection images are acquired without any moving components. The acquired images may be synthesized using a compressed sensing-based reconstruction algorithm to provide tomographic cross-sections of the imaged object from minimal number of images. Here, the angular step of X-ray scanning mainly depends on the distance between the X-ray sources in the source module. A finer angular step can be achieved using electronic, magnetic, or electrostatic steering of electron beams in each source. Compared to the 5th generation CT, in which electron beams are steered to hit the annular anode on the gantry, this component-level steering has the benefit of maintaining the overall system footprint to be much smaller and rendering the system to be robust upon failure of other components. Finally, using our unique source-detector arrangement, scattering information of the object can be acquired, which is not available in conventional CT, and dual-energy CT can be performed without fast electronics.

The described imaging approach, as described here, can be adopted in various technological fields, including medical X-ray imaging, baggage inspection system, and so on, and can be especially useful in resource-limited environments such as developing countries or battle field. The motion-free CT system described has several merits that can be largely summarized as follows:

(i) Compact motion-free CT: The biggest challenge in making a compact CT scanner arises from adopting a rotating gantry, which necessitates sophisticated slip rings and requires heavy electronics and high-voltage components to be revolved around the imaged object. Because about 1000 images are collected for each tomogram within a fraction of second, a conventional CT system also requires an X-ray source with high beam current, and thus large cooling requirement, and a detector with high frame rate. These requirements not only increase the cost, but also render the system bulky, complex, and easy to fail. Fifth generation CT designs have excluded a rotating gantry, but require steering of energetic electron beams along the circumference of gantry which circles around a patient. In addition, a full 360 degrees angle coverage is not achieved, and a large system footprint is required. By contrast, the systems and methods of the present disclosure overcome these limitations by arranging multiple sources and detectors in a novel way so that the projection images from full 360° angle can be acquired without any rotating components. Sequentially operating X-ray sources installed in a linear array therein, allows effective change of the illumination angle on the object. Electronic steering, together with a distributed array of detectors, enables CT scanning in a motion-free manner.

(ii) Robustness upon partial damage to the system: In existing scanners, critical functions are assigned to single components. For example, a single X-ray source emits X-rays, a single detector array records the image, and a slip ring installed on a rotating gantry changes the illumination angle of X-rays onto the object. Therefore, a failure in one of the components, which is highly probable, such as in a battlefield environment, which can lead to shutdown of the entire CT scanner. By contrast, a system, as disclosed herein, includes multiple modules, namely source and detector modules, to perform X-ray generation and image collection, effectively in parallel. Thus, upon damage to one or more of the distributed components, normal function may continue. In addition, damaged source and detector modules can be easily replaced.

(iii) Scattering information: In the diagnostic X-ray energy range (10 keV-150 keV), the interaction between X-rays and a material can be explained by photoelectric absorption, Thomson scattering, and Compton scattering. Conventional X-ray systems, including CT systems, record the attenuation of X-rays, while regarding the refraction or the angular deviation due to scattering as sources of noise. The present disclosure, however, recognizes that this scattering, contains rich information about the imaged object, which can be useful for distinguishing low-atomic-number materials such as soft tissues with high resolution and contrast. Therefore, using multiple detectors distributed along the circumference on the gantry, scattered X-ray beam components may be captured. With a proper reconstruction model, the scattered X-rays can be used to enhance soft tissue contrast, and boost the spatial resolution by canceling the smoothing effect due to scattering.

(iv) Dual-energy operation: Dual-energy CT, namely CT at two different X-ray energies, increases the detection sensitivity by providing material composition. For example, dual-energy CT can differentiate iodine from hemorrhage, which cannot be distinguished in single-energy CT, even when they are co-existent within the same region. Currently, dual-energy CT is performed using a rotating-gantry scanner in a way either to quickly switch the tube voltage of an X-ray source or to install two pairs of X-ray source and detector, which operate at different X-ray energies. Design of a system, in accordance with the present disclosure, can be easily modified for performing dual-energy CT by, say, alternatively placing two kinds of X-ray chips operating at different tube voltages, or alternatively using different anode materials. Projection images recorded at two tube voltages can then be combined using a compressed sensing-based reconstruction algorithm to provide a single volume characterized by two different material properties, e.g., atomic number and electron density.

Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A computed tomography (CT) imaging system comprising:
    a gantry having a bore for receiving a subject for imaging and defining a central axis extending along the bore and a radial plane extending transversely to the central axis extending along the bore;
    a plurality of source modules coupled to the gantry at fixed radial locations about the bore for directing X-ray beams toward the subject arranged in the bore and mounted at a slanted angle with respect to the radial plane;
    a plurality of detector modules coupled to the gantry at fixed radial locations about the bore and mounted at the slanted angle with respect to the radial plane such that one of the plurality of detector modules is arranged in diametric opposition to and on opposite sides of the radial plane of one of the plurality of source modules; and
    a control system configured to control the plurality of source modules to perform an imaging process with respect to the subject to receive CT image data from the plurality of detector modules.

2. The system of claim 1, wherein the one of the plurality of detector modules arranged in diametric opposition to and on opposite sides of the radial plane of the one of the plurality of source modules is offset along the central axis by a lateral distance.

3. The system of claim 1, wherein each of the plurality of source modules further comprises multiple X-ray source units arranged in a linear array.

4. The system of claim 1, wherein each of the plurality of source modules further comprises a source module controller.

5. The system of claim 1, wherein each of the plurality of detector modules further comprises shielding elements configured to control an X-ray contamination in proximate detector modules.

6. The system of claim 1, wherein each of the plurality of source modules further comprises a steering system for directing an electron beam generated therein.

7. The system of claim 6, wherein the steering system is configured to perform one of an electronic steering, a magnetic steering, and/or an electrostatic steering.

8. The system of claim 1, wherein the plurality of source modules are further configured to operate at one or more X-ray energy levels.

9. The system of claim 1, wherein each of the plurality of detector modules further comprises a curved detector.

10. The system of claim 1, wherein each of the plurality of detector modules further comprises an anti-scatter grid.

11. The system of claim 1, wherein each of the plurality of detector modules further comprises a detector module controller.

12. The system of claim 1, wherein the control system is further configured to capture a combination of attenuated and scattered components of X-ray energy from the subject using the plurality of detector modules.

13. The system of claim 1, further comprising a computer configured to perform a tomographic reconstruction process to generate one or more CT images using acquired CT image data.

14. The system of claim 13, wherein the computer is further configured to utilize a compressed sensing technique in the tomographic reconstruction process.

15. A system for performing computed tomography (CT) imaging of a subject, the system comprising:
    a gantry having a first and second circumference defining locations fixed in relation to a subject arranged therein, the first and second circumference being axially separated, and spaced from a central axial plane of the gantry;
    a plurality of source modules arranged at locations along the first circumference, and configured for directing X-ray beams toward the subject using a selected illumination pattern;
    a plurality of detector modules arranged at locations along the second circumference, wherein the source and detector modules are angled toward the central axial plane such that each source module is diametrically opposed to one or more detector modules; and
    a control system configured for controlling the plurality of source modules in accordance with the selected illumination pattern, and acquiring CT image data from the plurality of detector modules.

16. The system of claim 15, wherein each of the plurality of source modules further comprises multiple X-ray source units arranged in a linear array.

17. The system of claim 15, wherein each of the plurality of source modules further comprises at least one of: a source module controller; shielding elements configured for minimizing an X-ray contamination in proximate detector modules; and a steering system for directing an electron beam generated therein.

18. The system of claim 15, wherein the plurality of source modules are further configured to operate at one or more X-ray energy levels.

19. The system of claim 15, wherein each of the plurality of detector modules further comprises at least one of a curved detector or an anti-scatter grid.

20. The system of claim 15, wherein the control system is further configured to capture a combination of attenuated and scattered components of X-ray energy from the subject using the plurality of detector modules.

21. The system of claim 15, wherein the control system is further configured to concurrently operate the plurality of source modules to achieve a uniform illumination pattern.

22. The system of claim 15, wherein the control system is further configured to operate one or more of the plurality of source modules in a time-varying fashion.

* * * * *